US00PP12185P2

(12) United States Plant Patent
Skotak, Jr.

(10) Patent No.: US PP12,185 P2
(45) Date of Patent: Nov. 6, 2001

(54) AECHMEA PLANT NAMED 'INCA'

(75) Inventor: Chester Skotak, Jr., Alajuela (CR)

(73) Assignee: Deroose Plants BVBA, Evergem (BE)

( * ) Notice: Subject to any disclaimer, the term of this patent is extended or adjusted under 35 U.S.C. 154(b) by 0 days.

(21) Appl. No.: 09/419,912

(22) Filed: Oct. 18, 1999

(51) Int. Cl.[7] ..... A01H 5/00
(52) U.S. Cl. ..... Plt./370
(58) Field of Search ..... Plt./370

*Primary Examiner*—Bruce R. Campell
*Assistant Examiner*—June Hwu
(74) *Attorney, Agent, or Firm*—Foley & Lardner

(57) ABSTRACT

An Aechmea plant named 'Inca' characterized by having a compact plant shape and large inflorescence; wide, green, tongue-shaped foliage that is suffused with white-grey color; arched foliage which decreases from the bottom to the top of the plant; foliage that has no spines on the leafedge; large, long lasting, red-pink inflorescence which is heavily branched; and bracts with reddish-pink tinged tips on younger bracts and yellow tips on older bracts which make them distinctly visible.

1 Drawing Sheet

BACKGROUND OF THE INVENTION

The present invention comprises a new and distinct cultivar of Aechmea plant, hereinafter referred to by the cultivar name 'Inca'. The genus Aechmea is a member of the family Bromeliaceae.

Aechmea comprises a genus of more than 168 species of evergeen perennials suitable for cultivation in the home or in the greenhouse. Aechmea may be terrestrial or epiphytic. For the most part, the species vary in diameter from 12 to 18 inches to 3 or 4 feet and have rosettes of spiny-edged leaves.

Flowers and bracts of Aechmea frequently have brilliant colors and may last for several months. The range of colors for Aechmea is generally from the yellow through orange but may also include pink, orange, red and red-purple. Tubular, three-petalled flowers may also appear but are usually short-lived.

Aechmea may be advantageously grown as pot plants for greenhouse or home use. Typically, the plants are shaded from direct sunlight; and the central, vaselike part of the leaf rosette is normally filled with water.

Aechmea is native to tropical America. Leaves of Aechmea are usually formed as basal rosettes which are still and entire and in several vertical ranks. Aechmea has terminal spikes or panicles which are often bracted with petals united in a tube longer than the calyx.

Asexual propagation of Aechmea is frequently done through the use of tissue culture practices. Propagation can also be from offshoots which can be detached from the mother plant and grown in an appropriate soil or bark mixture. Methods for cultivating and crossing of Aechmea are well known.

The new cultivar is a product of a planned breeding program and was originated from a hybridization made during such a program in Balsa, Costa Rica in 1988. The female or seed parent was *Aechmea tessmanii*. The male or pollen parent was *Aechmea flavo rosea*×*Aechmea fasciata*(spineless form). 'Inca' was discovered and selected as a fowering plant within the progeny of the stated cross by the inventor, Chester Skotak, Jr., in 1995, in a controlled environment in Balsa, Costa Rica.

'Inca' is characterized by its spineless leaves and tall, reddish-pink inflorescence, which keeps its color for several months. 'Inca' is distinguishable from the female parent by its lack of spines, smooth foliage surface, and smaller habitus (50–55 cm) than *Aechmea tessmanii*. 'Inca' has shorter foliage (30–35 cm) than that of *Aechmea tessmanii* (50–70 cm). 'Inca' is distinguishable from the male parents by its lack of spines. 'Inca' has a smooth foliage surface and its inflorescence is heavily branched when compared to *Aechmea fasciata*. 'Inca' has a larger habitus than *Aechmea flavo rosea*.

Asexual reproduction of the new cultivar by tissue culture was performed by the inventor in a controlled environment in Balsa, Costa Rica in 1996, and has demonstrated that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be basic characteristics of 'Inca' which in combination distinguish this Aechmea as a new and distinct cultivar:

1. Compact plant shape and large inflorescence;
2. Wide, green, tongue-shaped foliage that is suffused with white-grey color;
3. Arched foliage which decreases from the bottom to the top of the plant;
4. Foliage that has no spines on the leaf edge;
5. Large, long lasting, red-pink inflorescence which is heavily branched; and
6. Bracts with reddish-pink tinged tips on younger bracts and yellow tips on older bracts which make them distinctly visible.

'Inca' has not been observed under all possible environmental conditions. The phenotype of the new cultivar may vary significantly with variations in environment such as temperature, light intensity, and daylength, without any change in genotype.

Of the many commercial cultivars known to the present inventor, the most similar in comparison to 'Inca' are the cultivars 'Friedericke' (U.S. Plant Pat. No. 5,872) and Aechmea plant named 'Maya' (U.S. pending Plant Pat. Ser. No. 09/419,913). The arch and shape of the leaves and the white-grey suffusion on the leaf-surface of 'Inca' are similar to those of 'Friedericke'. However, 'Friedericke' has a more compressed inflorescence whereas 'Inca' has a more developed inflorescence with a conical form. The color of the inflorescence of 'Inca' is red-pink with yellow accents whereas the inflorescence of 'Friedericke' is pinker in color. The basal bracts of 'Inca' cover one-third to one-half of the inflorescence, whereas the basal bracts of 'Friedericke' cover the whole inflorescence.

'Inca' and 'Maya' have a similar plant and leaf shape. However, the inflorescence of 'Inca' is more conical-shaped whereas the inflorescence of 'Maya' is more dome-shaped. The inflorescence of 'Inca' has a darker, red-pink color than the inflorescence of 'Maya'.

BRIEF DESCRIPTION OF THE DRAWING

The accompanying photographic illustration is a perspective view of the foliage and inflorescence of a typical 'Inca' plant, with colors being as true as possible with illustrations of this type.

DETAILED BOTANICAL DESCRIPTION

The following observations, measurements and values describe 12 month old plants grown in Evergem, Belgium, under greenhouse conditions which closely approximate those generally used in horticultural practice. Color references are made to The Royal Horticultural Society (R.H.S.) Colour Chart, except where general colors of ordinary significance are used.

Classification:

*Commercial.*—Aechmea cv. 'Inca'.

Parentage:

*Male parent.—Aechmea flavo rosea×Aechmea fasciata* (spineless form).

*Female parent.—Aechmea tessmanii.*

Propagation: Vegetative, by tissue culture.

Plant:

*Form.*—Funnel-form rosette.

*Height.*—Approximately 63 cm when flowering, including 13 cm pot and rootstock.

*Diameter.*—Approximately 60–65 cm.

*Growth habit.*—Upright.

*Vigor.*—The growing time of a commercial line out of a 50 cell pack to a blooming plant is 12 months.

Foliage:

*Shape.*—Ligulate, tongue-shaped, and strongly arching from the middle to the top. The arching decreases from the bottom to the top of the plant.

*Arrangement.*—Rosulate.

*Apex.*—Mucronate.

*Size.*—Approximately 30–50 cm long and 7–9 cm wide.

*Color.*—Sheath: Green (RHS 147B) suffused with white-grey (RHS 191B and C). Leaf brade: Upper leaf surface: Green (RHS 147A) suffused with grey (RHS 191C). Lower leaf surface: Green (RHS 137C), heavily suffused with grey (RHS 191D).

*Margin.*—Spineless.

*Veins.*—Not visible.

*Surface texture.*—Smooth (both upper and lower surfaces).

*Number of leaves.*—20 to 25 .

Inflorescence:

*Habit.*—Spike, conical-shaped, approximately 20–25 cm in diameter and 25 cm in height, approximately 20–22 spirally arranged bracts on the main stem.

*Main stem.*—Round, tomentose, approximately 30–35 cm long and 1 cm in diameter, red-pink (RHS 39A).

*Primary bracts.*—Longer than the bracts, reaching up to ⅓ to ½ inflorescence, approximately 5.5 to 12 cm long and 3–4 cm wide; the color of the upperside is red-orange (RHS 42A and B), the lower surface texture tomentose, upper surface texture glabrous, margin entire, acute to attenuate apex.

*Secondary stem.*—Oval to flattened, approximately 0.8 to 1.0 cm and 0.6 cm wide, red (RHS 39A), tomentose surface texture.

*Secondary bracts.*—Approximately 20 to 22 in number, approximately 2.5 to 3 cm long and 1–2 cm wide, yellow at the base (RHS 1C) and red at the top (RHS 42A and B); the bracts on the side have a more flattened form than the bracts on the top of the inflorescence, upper surface texture glabrous, lower surface texture tomentose, margins entire, elliptic shape, acute to attenuate apex.

*Flowers.*—1 per bract, many flowering at the same time. Petals: 3, base yellow, (RHS 4D), top is red-pink (RHS 38A), approximately 7–10 mm long and 3–4 mm wide, both upper and lower surface texture glabrous, margins entire, ovate to elliptic shape, acute to acuminate apex. Sepals: 3, white base more yellow to the top, approximately 8–13 mm long and 3–6 mm wide, both upper and lower surface texture glabrous, margins entire, ovate to elliptic shape, acute to acuminate apex. Stamens: 6 per flower, RHS 158A, approximately 5–10 mm long. Pistils: 1 per flower with 3 lobed stigma, RHS 158A, approximately 8–10 mm long.

Other significant characteristics: The inflorescence holds its color for approximately 5 to 6 months.

I claim:

1. A new and distinct Aechmea plant named 'Inca', substantially as illustrated and described herein.

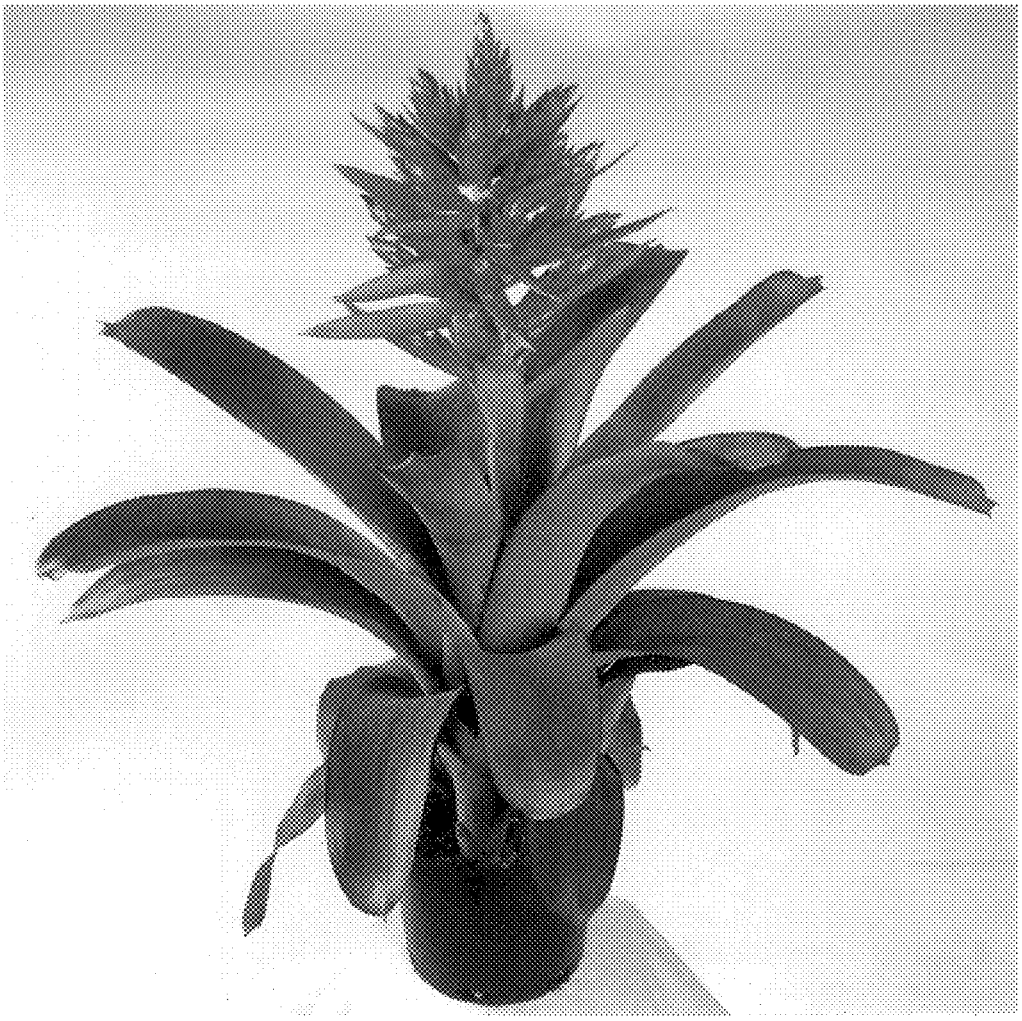

* * * * *